(12) United States Patent
Jung et al.

(10) Patent No.: US 8,933,295 B2
(45) Date of Patent: Jan. 13, 2015

(54) IDENTIFYING AGENTS TO TREAT ALZHEIMER'S DISEASE-RELATED DECREASED SORTING BEHAVIOR BY ADMINISTRATION TO A TRIPLE TRANSGENIC MOUSE EXPRESSING MUTANT FORMS OF APP, PRESENILIN OR TAU

(75) Inventors: Sun-Yung Jung, Radnor, PA (US); Mary Birchler, Malvern, PA (US)

(73) Assignee: Janssen Biotech, Inc., Horsham, PA (US)

( * ) Notice: Subject to any disclaimer, the term of this patent is extended or adjusted under 35 U.S.C. 154(b) by 519 days.

(21) Appl. No.: 12/993,480

(22) PCT Filed: Jun. 3, 2009

(86) PCT No.: PCT/US2009/046073
§ 371 (c)(1),
(2), (4) Date: Nov. 19, 2010

(87) PCT Pub. No.: WO2009/155133
PCT Pub. Date: Dec. 23, 2009

(65) Prior Publication Data
US 2011/0083200 A1    Apr. 7, 2011

Related U.S. Application Data

(60) Provisional application No. 61/074,437, filed on Jun. 20, 2008.

(51) Int. Cl.
*A01K 67/027* (2006.01)
*A01K 1/03* (2006.01)
*A01K 67/02* (2006.01)
*A61K 49/00* (2006.01)

(52) U.S. Cl.
CPC ............... *A01K 1/031* (2013.01); *A01K 67/02* (2013.01); *A61K 49/0008* (2013.01)
USPC .................................................. 800/3; 800/18

(58) Field of Classification Search
CPC ........... A01K 67/0275; A01K 2217/05; A01K 2227/105; A01K 2207/15; A01K 2217/00; A01K 5557/10; C12N 15/8509; G01N 2500/04; G01N 2500/10; G01N 33/57496
See application file for complete search history.

(56) References Cited

U.S. PATENT DOCUMENTS

| | | | |
|---|---|---|---|
| 5,877,399 | A | 3/1999 | Hsiao et al. |
| 5,898,094 | A | 4/1999 | Duff et al. |
| 2006/0153772 | A1 | 7/2006 | Jacobsen |
| 2007/0275957 | A1 | 11/2007 | Weiner et al. |

FOREIGN PATENT DOCUMENTS

WO    WO 03053136 A2    7/2003

OTHER PUBLICATIONS

Sigmund, CD (2000) Viewpoint: Are studies in genetically altered mice out of control? Arterioscler. Thromb. Vasc. Biol. 20: 1425-1429.*
Wall, RJ (1996) Transgenic livestock: Progress and prospects for the future. Theriogenology 45: 57-68.*
Neale et al., "The neurotransmitter N-acetylaspartyl-glutamate in models of pain, ALS, diabetic neuropathy, CNS injury and schizophrenia", Trends in Pharmacological Sciences, vol. 26, No. 9, pp. 477-484 (Sep. 2005).
Perna, Mark, "Nicotine Sensitization in a Rodent model of Schizophrenia; A Comparison of Adolescents, Adults, and Neurotrophic Factors", A thesis presented to the faculty department of psychology, East Tennessee State University, pp. 1-71 (May 2007).
Yacoubi et al., "Genetic rodent models of depression", Current Opinion in Pharmacology, vol. 7, pp. 3-7 (2007).
Buhr & White, "Difficult Behaviors in Long-Term Care Patients With Dementia", J. Amer. Med Dir Assoc., vol. 8: pp. e101-e113 (Mar. 2007).
Buhr & White, Difficult Behaviors in Long-Term Care Patients With Dementia, J. Amer. Med Dir Assoc., vol. 7: pp. 180-192 (2006).
Hsiao et al., "Correlative Memory Deficits, Aβ Elevation and Amyloid Plaques in Transgenic Mice", Science, vol. 274, pp. 99-102, (1996).
King & Arendash, "Behavioral characterization of the Tg2576 transgenic model of Alzheimer's disease through 19 months", Physiology & Behavior, vol. 75: pp. 627-642.
King & Arendash, "Maintained synaptophysin immunoreactivity in Tg2576 transgenic mice during agint: correlations with cognitive impairment", Brain Research, 926(1-2); pp. 58-68 (2002).
Larson, J. et al., "Alterations in synaptic transmission and long-term potentiation in hippocampal slices from young and agent PDAPP mice", Brain Research, 840, pp. 23-35 (1999).
Hsia, A.Y. et al., (1999), Proc. Natl. Acad. Sci. USA 96; pp. 3228-3233.
Chapman, P.P. et al., "Impaired synaptic plasticity and learning in aged amyloid precursor protein transgenic mice", Nat. Neurosci, 2; pp. 271-276, (1999).
Games et al., "Alxheimer-type neuropathology in transgenic mice overexpressing V717F β-amyloid precursor protein", Nature, (6514), vol. 373, pp. 523-527 (Feb. 9, 1995).
Fitzjohn et al., "Age-Related Impairment of Synpatic Transmission But Normal Long-Term Potentiation in Transgenic Mice that Overexpress the Human APP655SWE Mutant Form of Amyloid Precursor Protein", Journal of Neuroscience, 21(13), pp. 4691-4698.
Wong et al., "Genetically engineered mouse models of neurodegenerative diseases", Nat. Neurosci, vol. 5; pp. 633-639 (2002).

(Continued)

*Primary Examiner* — Deborah Crouch
(74) *Attorney, Agent, or Firm* — Brian C. Carey

(57) ABSTRACT

The method of the invention is useful for evaluating pharmaceutical compositions for treatment of neurological diseases encompassing neurological or neurodegenerative diseases associated with cognitive dysfunction and, in particular, dementia; schizophrenia; anxiety; depression; and pain using a rodent behavioral assay, wherein the method is useful in testing compositions useful in the modulation, amelioration, prevention, or treatment of dementia using a non-human animal carrying at least a transgene for human amyloid-beta protein or human tau and transgenes causing the elevated production of the human amyloid-beta protein in the animal as compared to nontransgenic animals of the same genetic background and the behavior is a nesting behavior.

6 Claims, 1 Drawing Sheet

(56) References Cited

OTHER PUBLICATIONS

Oddo et al., "Triple-Transgenic Model of Alzheimer's Disease with Plaques and Tangles: Intracellular Aβ and Synaptic Dysfunction", Neuron, 39; pp. 409-421 (2003).

Oddo et al., "Amyloid deposition preceds tangle formation in a triple transgenic model of Alzheimer's disease", Neurobiology of Aging 24; pp. 1063-1070 (2003a).

Billings et al., "Intraneuronal Aβ Causes the Onset of Early Alzheimer's Disease-Related Cognitive Deficits in Transgenic mice", Neuron vol. 45; pp. 675-688 (2005).

Giminez-Llort et al., "Model behavioral and neuronal symptoms of Alzheimer's disease in mice: a role for intraneuronal amyloid", Neuroscience and BioBehavior Reviews, vol. 31; pp. 125-147 (2007).

Gröticke et al., "Behavorial alternations in the pilocarpine model of temporal lobe epilepsy in mice", Experimental Neurology, vol. 207(2); pp. 329-349 (2007).

Kohda K., et al., "Glucocorticoid Receptor Activation Is Involved in Producing Abnormal Phenotypes of Single-Prolonged Stress Rats: A Putative Post-Traumatic Stress Disorder Model", Neuroscience 148(1); pp. 22-33 (2007).

Crawley, J.N., "Behavioral phenotyping of transgenic andknockout mice: experimental design and evaluation of general health, sensory functions, motor abilities, and specific behavioral tests", Brain Research Interactive, 835(1); pp. 18-26 (1999).

Hatcher et al., "5-HT6 Receptor Antagonists Improve Performance in an Attentional Set Shifting Task in Rats", Psychopharmacology, 181(2); pp. 253-259, (Sep. 2005).

Paolo et al., "Utility of a Wisconsin Car Sorting Test Short Form in Persons with Alzheimer's and Parkinson's Disease", J. Clin Exp Neuropsychol., vol. 18(6) pp. 892-897 (Dec. 1996).

Gordon et al., Correlation between Cognitive Deficits and Ab Deposits in Transgenic APPplusPS1 Mice Neurobiology of Aging, vol. 22(3), pp. 377-386 (May-Jun. 2001).

Janus et al., "Transgenic mouse models of Alzheimer's disease", Physiology & Behavior, vol. 73, pp. 873-886 (2001).

International Search Report for PCT/US09/46074 dated Sep. 2, 2007.

* cited by examiner

SEQUENCE LISTING

```
<160> NUMBER OF SEQ ID NOS: 4

<210> SEQ ID NO 1
<211> LENGTH: 770
<212> TYPE: PRT
<213> ORGANISM: Homo Sapiens

<400> SEQUENCE: 1

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160
```

-continued

```
Lys Ser Thr Asn Leu His Asp Tyr Gly Met Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
                340                 345                 350

Thr Gln Glu Pro Leu Ala Arg Asp Pro Val Lys Leu Pro Thr Thr Ala
            355                 360                 365

Ala Ser Thr Pro Asp Ala Val Asp Lys Tyr Leu Glu Thr Pro Gly Asp
370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
            405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
            435                 440                 445

Glu Arg Gln Gln Leu Val Glu Thr His Met Ala Arg Val Glu Ala Met
            450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
            485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
            515                 520                 525

Gln Val Met Thr His Leu Arg Val Ile Tyr Glu Arg Met Asn Gln Ser
            530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
            565                 570                 575
```

```
Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
            595                 600                 605

Val Asn Gly Glu Phe Ser Leu Asp Asp Leu Gln Pro Trp His Ser Phe
        610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770

<210> SEQ ID NO 2
<211> LENGTH: 467
<212> TYPE: PRT
<213> ORGANISM: Homo Sapiens

<400> SEQUENCE: 2

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175
```

```
Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
            290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
            355                 360                 365

Leu Ala Gly Glu Asp Pro Glu Glu Arg Gly Val Lys Leu Gly Leu Gly
            370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
450                 455                 460

Phe Tyr Ile
465

<210> SEQ ID NO 3
<211> LENGTH: 448
<212> TYPE: PRT
<213> ORGANISM: Homo Sapiens

<400> SEQUENCE: 3

Met Leu Thr Phe Met Ala Ser Asp Ser Glu Glu Val Cys Asp Glu
  1               5                  10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
```

-continued

```
               65                  70                  75                  80

Leu Lys Tyr Gly Ala Lys His Val Ile Met Leu Phe Val Pro Val Thr
                85                  90                  95

Leu Cys Met Ile Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
            115                 120                 125

Pro Ser Val Gly Gln Arg Leu Leu Asn Ser Val Leu Asn Thr Leu Ile
130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
            195                 200                 205

Trp Asn Phe Gly Ala Val Gly Met Val Cys Ile His Trp Lys Gly Pro
210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
            275                 280                 285

Phe Pro Ala Leu Ile Tyr Ser Ser Ala Met Val Trp Thr Val Gly Met
290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
            355                 360                 365

Phe Tyr Ser Val Leu Val Gly Lys Ala Ala Thr Gly Ser Gly Asp
370                 375                 380

Trp Asn Thr Thr Leu Ala Cys Phe Val Ala Ile Leu Ile Gly Leu Cys
385                 390                 395                 400

Leu Thr Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
            435                 440                 445
```

<210> SEQ ID NO 4
<211> LENGTH: 758
<212> TYPE: PRT
<213> ORGANISM: Homo Sapiens

<400> SEQUENCE: 4

```
Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
             115                 120                 125

Gly Lys Val Val Gln Glu Gly Phe Leu Arg Glu Pro Gly Pro Pro Gly
         130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
             195                 200                 205

Lys Glu Arg Pro Gly Ser Lys Glu Glu Val Asp Glu Asp Arg Asp Val
         210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
                260                 265                 270

Ser Lys Val Ser Thr Glu Ile Pro Ala Ser Glu Pro Asp Gly Pro Ser
             275                 280                 285

Val Gly Arg Ala Lys Gly Gln Asp Ala Pro Leu Glu Phe Thr Phe His
         290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
             355                 360                 365

Ser Arg Val Pro Gln Leu Lys Ala Arg Met Val Ser Lys Ser Lys Asp
         370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
```

-continued

|   |   |   | 420 |   |   | 425 |   |   | 430 |   |   |
|---|---|---|---|---|---|---|---|---|---|---|---|
| Pro | Glu | Pro 435 | Pro | Ser | Ser | Pro 440 | Lys | His | Val | Ser 445 | Ser | Val | Thr | Ser | Arg |
| Thr | Gly 450 | Ser | Ser | Gly | Ala 455 | Lys | Glu | Met | Lys 460 | Leu | Lys | Gly | Ala | Asp | Gly |
| Lys 465 | Thr | Lys | Ile | Ala 470 | Thr | Pro | Arg | Gly 475 | Ala | Ala | Pro | Pro 480 | Gly | Gln | Lys |
| Gly | Gln | Ala | Asn 485 | Ala | Thr | Arg | Ile 490 | Pro | Ala | Lys | Thr 495 | Pro | Pro | Ala | Pro |
| Lys | Thr | Pro 500 | Pro | Ser | Ser | Gly 505 | Glu | Pro | Pro | Lys 510 | Ser | Gly | Asp | Arg | Ser |
| Gly | Tyr | Ser 515 | Ser | Pro | Gly | Ser 520 | Pro | Gly | Thr | Pro 525 | Gly | Ser | Arg | Ser | Arg |
| Thr | Pro | Ser 530 | Leu | Pro | Thr | Pro 535 | Pro | Thr | Arg | Glu 540 | Pro | Lys | Lys | Val | Ala |
| Val 545 | Val | Arg | Thr | Pro | Pro 550 | Lys | Ser | Pro | Ser 555 | Ser | Ala | Lys | Ser | Arg 560 | Leu |
| Gln | Thr | Ala | Pro 565 | Val | Pro | Met | Pro 570 | Asp | Leu | Lys | Asn 575 | Val | Lys | Ser | Lys |
| Ile | Gly | Ser | Thr 580 | Glu | Asn | Leu | Lys 585 | His | Gln | Pro | Gly 590 | Gly | Gly | Lys | Val |
| Gln | Ile | Ile 595 | Asn | Lys | Lys | Leu 600 | Asp | Leu | Ser | Asn 605 | Val | Gln | Ser | Lys | Cys |
| Gly | Ser | Lys 610 | Asp | Asn | Ile | Lys 615 | His | Val | Pro | Gly 620 | Gly | Gly | Ser | Val | Gln |
| Ile 625 | Val | Tyr | Lys | Pro | Val 630 | Asp | Leu | Ser | Lys 635 | Val | Thr | Ser | Lys | Cys 640 | Gly |
| Ser | Leu | Gly | Asn 645 | Ile | His | His | Lys 650 | Pro | Gly | Gly | Gly 655 | Gln | Val | Glu | Val |
| Lys | Ser | Glu 660 | Lys | Leu | Asp | Phe 665 | Lys | Asp | Arg | Val 670 | Gln | Ser | Lys | Ile | Gly |
| Ser | Leu | Asp 675 | Asn | Ile | Thr | His 680 | Val | Pro | Gly | Gly 685 | Gly | Asn | Lys | Lys | Ile |
| Glu | Thr 690 | His | Lys | Leu | Thr 695 | Phe | Arg | Glu | Asn 700 | Ala | Lys | Ala | Lys | Thr | Asp |
| His 705 | Gly | Ala | Glu | Ile | Val 710 | Tyr | Lys | Ser | Pro 715 | Val | Val | Ser | Gly | Asp 720 | Thr |
| Ser | Pro | Arg | His 725 | Leu | Ser | Asn | Val 730 | Ser | Ser | Thr | Gly 735 | Ser | Ile | Asp | Met |
| Val | Asp | Ser | Pro 740 | Gln | Leu | Ala | Thr 745 | Leu | Ala | Asp | Glu 750 | Val | Ser | Ala | Ser |
| Leu | Ala | Lys | Gln 755 | Gly | Leu |

IDENTIFYING AGENTS TO TREAT ALZHEIMER'S DISEASE-RELATED DECREASED SORTING BEHAVIOR BY ADMINISTRATION TO A TRIPLE TRANSGENIC MOUSE EXPRESSING MUTANT FORMS OF APP, PRESENILIN OR TAU

CROSS-REFERENCE TO RELATED APPLICATIONS

This application claims the benefit of International Application Number PCT/US2009/046073, filed 3 Jun. 2009, which claims the benefit of U.S. Provisional Application No. 61/074,437, filed 20 Jun. 2008. The entire contents of each of the aforesaid applications are incorporated herein by reference in their entirety.

BACKGROUND

The methods disclosed herein relate to rodent models of human disease. Specifically, the described and claimed subject matter relate to methods of characterizing potential therapeutics for efficacy for use in treating, preventing, or ameliorating pathological conditions associated with specific mental symptoms such as dementia, depression, or apathy using a method of scoring behavior-related symptoms in a rodent model.

Numerous physical disorders produce behavioral or mental symptoms such as dementia, anxiety, apathy, depression, and personality changes. Alzheimer's disease (AD), the most common neurodegenerative disorder and cause of senile dementia, is the target of intense clinical and basic research efforts as there is presently neither a predictor or cure. In addition to cognitive deficits, AD patients experience "behavioral and psychological symptoms of dementia" (BPSD), including, sleep disturbances, paranoia, aggression, and anxiety. These symptoms often manifest before cognitive deficits are apparent and cause significant distress both to patients and caregivers (Buhr & White, 2007. J Amer Med Dir Assoc 8:e101-113; Buhr & White 2006. J Amer Med Dir Assoc 7:180-192).

Efforts have been made to develop animal models which exhibit the pathophysiological hallmarks of the disease, such extracellular β-amyloid-rich plaques and intraneuronal neurofibrillary tangles (NFTs); however, behavioral correlates between mouse and man are difficult. Attempts to characterize behavioral deficits in these models include tests of curiosity and apathy (Boissier's hole-board test), lack of ability to cope with mild stressors (white-black box), and increased emotionality (freezing behavior). These studies have provided some insight into the behavioral manifestations of these models; however, conducting behavioral tests requires specialized equipment and training, and can be very labor intensive. Therefore, an easily identifiable behavioral marker of disease in an animal model is desired by those skilled in the art.

SUMMARY OF THE INVENTION

The invention relates to unique tests in rodents related to nesting behavior that provides an expedient, operator-independent method of gauging the efficacy of treatments to modulate or ameliorate pathologies associated with behavioral symptoms.

In one embodiment, the invention is a method of identifying or evaluating a test agent or a composition for use in the prevention, treatment, or amelioration of behavioral symptoms associated with a neurological disorder in a human patient comprising, the use of rodents that through the expression of transgenes, due to inbreeding or outbreeding, or through other physical lesion or environmental conditioning or stimuli, exhibit decreased innate nesting behavior manifested by the propensity to sort bedding material into distinct areas of nestable material and non-nestable material by observing the increase in the sorting behavior in groups of the behavior exhibiting mice upon administration of the composition and comparing those treated animals with untreated control animals. Test agents may then be selected based on the sorting behavior observations. In one aspect of the invention, the sorting behavior is recorded as a numerical score and the score for different groups of rodents is treated statistically to determine whether the effects of the composition on the behavior is statistically different between groups of mice.

In another embodiment, groups of rodents exhibiting some level of sorting behavior are administered a compound or control, subjected to a treatment, or given a modified diet and the increase or decrease in sorting behavior is observed and/or scored.

This novel behavior test may be used to assess the efficacy, utility, and/or side effects of large or small molecule therapeutics that may have impact on the biochemical pathways involved in neurodegenerative disorders that affect behavioral and/or psychological symptoms of dementia.

BRIEF DESCRIPTION OF THE DRAWING

FIG. 1 shows photographs of cages of mice that A) have sorted bedding components; or B) not sorted bedding components.

DETAILED DESCRIPTION OF THE INVENTION

Abbreviations

"Abs" antibodies, polyclonal or monoclonal; "A-beta" amyloid beta protein; "APP" amyloid precursor protein; "Ig" immunoglobulin; "Mab" monoclonal antibody; "BPSD" behavioral and psychological symptoms of dementia; "FAD" familial Alzheimer's disease; "APP$_{Swe}$", K670N-M671L or KM→ML Swedish double mutant of APP; "NFT" neurofibrillary tangles; "PS" presenilin; "Tg" transgenic.

Definitions

By "A-beta", "Aβ", "amyloid", "beta amyloid", "amyloid beta protein" is meant the 39-43 residue long fragments derived from proteolytic cleavage of beta-amyloid precursor protein (APP).

By "amyloid precursor protein" or "APP" and also known as "Amyloid beta A4 protein precursor" (APP or AβPP) or the "Alzheimer disease amyloid protein" is meant the human protein produced as a single polypeptide of 770, 751, 695 or 693 amino acids, or as described in UniProt Accession Record, P05067. Genetic variants causing FAD have been described and include the "Swedish double mutant" (APP K670N-M671L or KM→ML), the "London" FAD mutation (V642I), "London" V717I, V717F; "Flemish" (APP/A692G) and "Dutch" (APP/E693Q), I716V, N694D, A713T and others. Transgenic mice expressing one or more of these human protein variants have been created to study the effects of these mutations individually and in combination (See e.g., Janus, C., Westaway, D. (2001) Physiology & Behavior 73(5), pp 873-886).

By "PS" is meant presenilin and by PS1 is meant presenilin-1 (PSEN1, AD3, FAD, Presenilin-1, Protein S182, PSNL1, S182) gene (NCBI Gene 5663) coding for a 467 amino acid protein. Most autosomal dominant inherited forms of early onset Alzheimer's disease (AD) are caused by mutations in the presenilin-1 (PS-1) gene on chromosome 14 such as M146L or L286V. By PS2 is meant the presenilin-2 (AD3L, AD3LP, AD4, AD5, E5-1, Presenilin-2, PSNL2, STM2, STM-2) a gene (NCBI Gene 5664) coding for one of two splicing variants of presenilin-2. Presenilins are postulated to regulate APP processing through their effects on gamma-secretase, an enzyme that cleaves APP.

By "tau" or "tau protein" is meant the microtubule-associated (MAP) protein also known as "neurofibrillary tangle protein", "paired helical filament-tau" (PHF-tau). Human tau is typified by the sequence given in the NCBI Accession Record, P10636, as a 758 residue protein and variants and isoforms thereof.

By "transgenic", "Tg" or a "transgenic animal" is meant an animal comprising a non-endogenous, exogenous genetic element or gene that has been stably and/or heritably integrated into the genetic material of the animal and causes the exogenous gene to be expressed in specific or substantially all of the cells, tissues or organs of the animal, such that the biochemical effects of the encoded protein on the reproduction, embryogenesis, maturation, aging, physiology or metabolism of the animal can be assessed. Transgenes may integrate randomly into chromosomal DNA and are transmitted as a Mendelian trait. Targeting of transgene expression to different cell types is achieved with the use of fusion gene constructs in which a coding sequence of interest is placed downstream of a cell-specific promoter and upstream of a polyadenylation [p(A)] signal sequence. The fusion gene construct is then microinjected into one of the pronuclei of fertilized mouse eggs, which are subsequently implanted in the oviduct of pseudopregnant recipient mice. Progeny are analyzed for transgene integration and positive mice subsequently mated, their offspring screened for transgene expression and, where positive, used to develop transgenic lines with stable integration and expression of the transgene. In some cases and transgenic mouse may also be a "knock-out." A knockout mouse is a genetically engineered mouse in which one or more genes have been turned off through a gene inactivation usually by a directed homologous recombination technique with an inoperable gene construct in an embryonic stem cell.

As used herein the term "modulating, ameliorating, or treating" includes prophylaxis of a physical and/or mental condition or amelioration or elimination of the developed physical and/or mental condition once it has been established or alleviation of the characteristic symptoms of such condition.

By "SAT" is meant the sorting activity test of the invention.

Diseases

The methods described and claimed herein are useful for evaluating pharmaceutical agents and compositions for treatment of pathophysiologically related behavioral symptomology of several neurological diseases including neurodegenerative diseases, schizophrenia, anxiety, depression, and pain. Neurodegenerative diseases include sporadic Alzheimer's pre-senile and senile dementia (AD), familial Alzheimer's disease (FAD), Down's syndrome (DS), hereditary motor and sensory neuropathies (HMSN, also known as Charcot-Marie-Tooth disease), diabetic polyneuropathy, Lewy body diseases such as Parkinson's disease with or without dementia, Lewy body variant of Alzheimer's disease (LBVAD), corticobasal degeneration (CBD), progressive supranuclear palsy (PSP), neuronal intermediate filament disease (NFID), Pick's disease (PiD), olivopontocerebellar atrophy, Huntington's disease (HD), amyotrophic lateral sclerosis (ALS), age-onset neurological deterioration (age-related dementia), mild cognitive impairment (MCI), vascular dementia (such as due to infarction or arteritis), alcoholic polyneuropathy, tinnitus, multiple sclerosis, tau-mediated neurodegenerative diseases, that is, disease associated with tau pathology or "tauopathies" such as frontotemporal dementias (FTDs) in addition to AD, as well as analogous veterinary disease states. Other physical disorders may lead to mental symptoms of dementia, inattention, delirium, depression, anxiety, mood alterations and poor concentration or apathy including hyperthyroidism, hypothyroidism, epilepsy, subdural hematoma, Cushing's syndrome, and Diabetes mellitus. Certain infections that attack the nervous system of such as HIV/AIDS, herpes, syphilis, and Lyme disease may also cause mental symptoms and behavioral changes. In addition, certain mental disorders of unknown or complex etiology such as schizophrenia, obsessive-compulsive disorder (OCD), panic disorder, post-traumatic stress disorder (PTSD), social phobia or social anxiety disorder, and various forms of depression; including major depressive disorder, dysthymic disorder or dysthymia, psychotic depression, seasonal affective disorder (SAD) manifest behavioral changes. Pain, particularly, chronic pain and neuropathic pain may lead to depression and pain patients manifest behavioral symptoms. Thus, treatments which may have any basis for ameliorating, curing, reversing or modifying the above described conditions leading to behavioral symptoms may be tested by the method of the invention in rodents.

Alzheimer's disease (AD) is a degenerative disorder of the brain first described by Alois Alzheimer in 1907 after examining one of his patients who suffered drastic reduction in cognitive abilities and had generalized dementia. It is the leading cause of dementia in elderly persons. AD patients have increased problems with memory loss and intellectual functions which progress to the point where the individual is not capable of independent living. With the loss of cognitive function, the patients exhibit behavioral and personality changes, socially inappropriate actions and schizophrenia.

Common features in the brain of patients with Alzheimer's disease include the presence of abundant intraneuronal neurofibrillary tangles (NFTs) and extracellular $\beta$-amyloid (A$\beta$)-rich plaques. NFTs are cytoskeletal pathologies largely composed of aggregates of hyperphosphorylated microtubule-associated tau proteins assembled into fibers called paired helical filaments (PHFs) and can cause neuronal or glial inclusions. Large numbers of $\beta$-amyloid (A$\beta$)-containing neuritic plaques are found in the neocortex and hippocampus, along with progressive cognitive impairment. In a small percentage of cases, AD results from inheritance of an autosomal dominant mutation in the amyloid precursor protein (APP). The major component of amyloid plaques is a peptide, a small 39-43 amino acid long $\beta$-amyloid peptide that is generated from the cleavage of the large amyloid precursor protein (APP).

Mutations causing increased production of the 42 amino acid form of $\beta$-amyloid peptide have been genetically linked to autosomal dominant familial forms of Alzheimer's diseases (FAD). Known missense mutations affect codon 717 of APP (altering V717I "London", V717G and V717F in the polypeptide), while codons 670/671 (altering K670N and M671L in the polypeptide) are referred to as the Swedish mutation. Other APP variants have been termed Flemish (APP/A692G) and Dutch (APP/E693Q). All these mutations affect the proteolytic processing of APP yielding more amyloidogenic peptides. APP can be processed by at least three enzymes known as secretases: alpha-, beta-, and gamma-secretases. Beta-secretase (BACE) initiates A$\beta$ peptide generation by cleaving APP after methionine 671 (APP770 numbering) leading to a 12 kD retained membrane carboxyterminal fragment (Citron M, Teplow D B, Selkoe D J. 1995, Generation of amyloid beta protein from its precursor is sequence specific. Neuron. 14:661 70). The 12 kD fragment may then undergo gamma-secretase cleavage within the hydrophobic transmembrane domain to release the 40, 42, or 43 residue A-beta peptides (Seubert P, Vigo-Pelfrey C, Esch F, Lee M, Dovey H, Davis D, Sinha S, Schlossmacher M, Whaley J, Swindlehurst C. Isolation and quantification of soluble Alzheimer's beta-peptide from biological fluids. Nature. 1992 359: 325 7).

Presenilins are membrane proteins associated with intracellular high molecular weight protein complexes that are involved in the processing of APP to the Aβ peptide.

Diffuse plaques comprising almost exclusively of β-amyloid peptides may form in AD, however, amyloid plaques typically contain numerous associated cellular products. Deposits of β-amyloid occur very early in the disease process, long before clinical symptoms develop. Because these mutations appear to be pathogenic and cause Alzheimer's diseases in transgenic mice, β-amyloid is widely believed to play a causal role in the disease and is a key feature of the post-mortem diagnosis. Attempts have been made to develop diagnostic imaging methods to detect amyloid plaques as a convenient marker for early diagnosis and prevention of the disease as well as a method for monitoring the effectiveness of therapeutic regimens.

Neuritic beta-amyloid containing plaques and NFTs, composed of filamentous aggregates of hyperphosphorylated tau protein are one aspect of the neuropathology of AD. Synapse loss in frontal cortex biopsies in AD correlate with cognitive severity. Notably, the memory and cognitive decline observed in AD patients correlates better with the synaptic pathology than either plaques or tangles (Terry, R. D. et al., (1991). Physical basis of cognitive alterations in Alzheimer's disease: synapse loss is the major correlate of cognitive impairment, Ann. Neurol. 30, 572-80; Dickson, D. W. et al., (1995) Correlations of synaptic and pathological markers with cognition of the elderly, Neurobiol. Aging 16, 285-98; Sze, C. I. et al., (1997) Loss of the presynaptic vesicle protein synaptophysin in hippocampus correlates with cognitive decline in AD (Masliah, E. et al., (2001) Altered expression of synaptic proteins occurs early during progression of Alzheimer's disease, Neurology 56, 127-9), and is likely the most significant factor contributing to the initial stages of memory loss (Selkoe, D. J. (2002) Alzheimer's disease is a synaptic failure, Science 298, 789-91).

Description of Alzheimer Disease Mouse Models

A number of transgenic mouse lines expressing human (Hu) APP695 (both wild-type and mutated forms associated with FAD) as well as mouse wild-type APP genes have been generated using various inbred mouse strains such as FVB/N, C57BL/6J, 129, DBA, C3H to name a few. HuAPP695.SWE Tg mice have also been created on a C57BL/6×C57BL/6// SJL mouse genetic background such as Tg2576. The Tg2576 transgenic line which was developed through insertion of the hAPP695 construct with the 'Swedish' double mutation and hamster prion protein cosmid vector into a C57BL6/J×SJL host (U.S. Pat. No. 5,877,399; Hsiao et al., (1996) Science 274:99-102).

The Tg2576 expressed HuAPP Swedish mutation at a level 5.6-fold greater than the endogenous brain APP, and showed longevity comparable to their non-Tg littermates. In addition to AD-type pathology, Tg2576 shows cognitive impairment as measured by spontaneous alternation in a "Y" maze and spatial memory in a water maze suggesting that the manipulation of APP affects cognitive function in addition to pathology. King and Arendash (2002. Physiol Behavior 75:627-42; 2002 Brain Research 926(1-2): 58-68) reported behavioral changes in the Tg2576 mouse such as less burrowing activity. However, many APP gene transgenic mice do not produce or have weak FAD pathology suggesting that these AD models are unable to produce sufficient amounts of A-beta in the brain to initiate Alzheimer's related pathology.

Duff and Hardy, U.S. Pat. No. 5,898,094, describe the production of a double transgenic mouse expressing APPK670N, M671L and a mutant presenilin transgene. Doubly transgenic mice from a cross between Tg mice expressing HuAPP Swedish mutation, Tg(HuAPP695.K670N-M671L) 2576, and a mutant HuPS1 gene, Tg(M146L) develop visible Aβ deposits in hippocampus and cerebral cortex at earlier ages (6-16 weeks) than their single transgenic Tg2576 littermates. Both the single knock-in, Tg2576, and the double, Tg2576+PS1 transgenic, exhibit progressive Aβ neuritic plaque formation, dystrophic neurites, and neuroinflammatory involvement of AD.

Gene-targeted and transgenic mice have proven to be invaluable for addressing some of the mechanisms underlying the synaptic dysfunction (Larson, J., et al., (1999) Alterations in synaptic transmission and long-term potentiation in hippocampal slices from young and aged PDAPP mice, Brain Res. 840, 23-35; Hsia, A. Y. et al., (1999) Plaque-independent disruption of neural circuits in Alzheimer's disease mouse models, Proc. Natl. Acad. Sci. U.S.A. 96, 3228-33; Chapman, P. P. et I al. (1999). PDAPP Tg mice display human $APP_{V717F}$ under the PDGFβ promoter, Games D, Adams D, Alessandrini R, Barbour R, Berthelette P, Blackwell C, Carr T, Clemens J, Donaldson T, Gillespie F. Alzheimer-type neuropathology in transgenic mice overexpressing V717F beta-amyloid precursor protein. Nature. 1995 Feb. 9; 373(6514): 523-7. Impaired synaptic plasticity and learning in aged amyloid precursor protein transgenic mice, Nat. Neurosci. 2, 271-6; Pitzjohn, S. M. et al., (2001) Age-related impairment of synaptic transmission but normal long-term potentiation in transgenic mice that overexpress the human $APP_{695}SWE$ mutant (J. Neurosci. 21, 4691-8), although none of these models recapitulate both hallmark pathological lesions (Wong, P. C., et al., (2002) Genetically engineered mouse models of neurodegenerative diseases, Nat. Neurosci. 5, 633-9).

A triple transgenic (3×Tg-AD) mouse was developed by LaFerla et al., at the University of California at Irvine (WO2003053136A2, Oddo et al., Neuron (2003) 39: 409-421). This mouse is commonly used as a rodent model of Alzheimer's disease. To create the mice, single cell embryos were harvested from mutant homozygous PS $1_{M146V}$ knock-in mice. Using the pronuclear microinjection technique, two independent transgenic constructs encoding human $APP_{Swe}$ and four-repeat tau without N-terminal (4R0N), under the control of the mouse Thy1.2 regulatory elements, were co-microinjected. The injected embryos were re-implanted into foster mothers and the resulting offspring genotyped to identify 3×Tg-AD mice. The 3×Tg-AD mice, thus, harbor mutations in three different genes: the beta-amyloid precursor protein (beta-$APP_{SweKM \rightarrow NL}$), presenilin-1 ($PS1_{M146V}$) and tau (P301L). This model reportedly shows both plaque and tangle pathology in brain regions relevant to Alzheimer's disease, such as hippocampus and cortex. Intracellular Abeta immunoreactivity has been reported to appear by three months of age and extracellular A-beta deposits between six and 12 months of age (Oddo et al., Neurobiol Aging (2003a), 24: 1063-1070; Oddo et al., Neuron (2003) 39: 409-421).

The triple transgenic (3×Tg-AD) mouse model, has been reported to show long-term and short-term cognitive deficits (Billings et al, 2005 Neuron 45:675-688; Giminez-Llort et al., 2007, Neuroscience Behavior. Rev. 31: 125-147). These deficits appear by six months of age, before A-beta and tau pathology is evident, and become more severe over time. Attempts to characterize BPSD in this model have shown diminished curiosity and apathy (Boissier's hole-board test), lack of ability to cope with mild stressors (white-black box), and increased emotionality (freezing behavior, Giminez-Llort et al., 2007). These behaviors manifest at an early age, and become more severe over time.

A novel behavior was made in the 3×Tg-AD mouse model of Alzheimer's disease. From an early age, 3×Tg-AD mice do not exhibit the typical "sorting" behavior observed in wild-type and other transgenic mice when housed with mixed-type bedding, such as AlphaCobb®. Applicants have not observed loss of sorting behavior in the Tg2576 transgenic mouse model in the same time frame but other rodents or rodent models of neurological disorders due to genetic manipulation, disease, or environment may be expected to exhibit more or less sorting behavior which may be useful in the method of the invention.

Animal Models of Diseases Associated with Altered Behavior

Animal models of pain in which neuroactive agents can be tested include inflammatory pain caused by injection of formalin or carrageenan in the footpad and neuropathic pain caused by chronic ligation of the sciatic nerve.

Diabetic sensory neuropathy can be mimicked in rodents by ischemia-induced excitatoxicity in the adult or neonatal-brain. Traumatic brain injury can be invoked by percussive trauma and spinal cord injury by a controlled-force crush.

Schizophrenia can be induced by phencyclidine (PCP) exposure.

Amyotropic Lateral Sclerosis (ALS) is mimicked by superoxide dismutase 1 transgenic mice.

Animal models of epilepsy, such as the pilocarpine model of acquired epilepsy, are useful to study the relationship between epilepsy and behavioral dysfunctions. Epilepsy is a disease characterized by frequent comorbidities in patients which comprise major depression, anxiety disorders, psychosis and cognitive dysfunction. In order to ensure the occurrence of status epilepticus (SE), dosing of pilocarpine can be increased until onset of SE and terminated by diazepam after either 60, 90 or 120 min. Mice that survive SE developed epilepsy (Gröticke et al., 2007. Exper Neurol 207(2): 329-349).

Post-traumatic stress disorder (PTSD) is a stress-related mental disorder caused by experience of a traumatic event, and presents with characteristic symptoms including intrusive memories (flashback), hyperarousal, and avoidance. Rats exposed to single-prolonged stress (SPS) showed enhanced inhibition of the HPA system and can be used as an animal model of PTSD (Kohda, K. et al., 2007 Neuroscience 148(1): 22-33). SPS consisted of 2-hour restraint in an confining acrylic animal holder (55×45×200 mm) followed by 20-min forced-swimming (25° C.) and ether anesthesia.

Animals can be outbred or inbred to exaggerate certain behaviors (see e.g., Yacoubi and Vaugeois, 2007 Curr Opin Pharac. 7:3-7). Mice were selectively bred for high and low immobility on the tail suspension test (TST). After ten generations of breeding, helpless (H/Rouen) CD-1 mice spent 200 sec immobile in a six-minute TST whereas the non-helpless (NH/Rouen) mice spent less than 7 sec. Various levels of neurotransmitter receptors (5-HT1A) and sleep abnormalities validate the H/Rouen mouse as a model of depression. Swim Low-Active (SwLo) rats were selectively bred Sprague-Dawley rats for low activity in the forced swim test (FST) whereas Swim High-Active (SwHi) rats are more active. These rats have been shown to respond to antidepressant treatment. High-anxiety-related behavior (HAB) was selectively bred in CD1 mice as well as their counterparts, low-anxiety behavior (LAB). These mice appear to model the comorbidities of depression and anxiety. In another example male outbred rats, selectively mated for high anxiety-related behavior (HAB) or displaying low-anxiety-related behavior (LAB) can be selected with regards to their anxiety-related behavior using e.g., the elevated plus-maze test and mated to establish the line now termed HAB. These animals can be used for pain testing. Paw withdrawal latencies to heat are significantly increased in HAB animals.

These and other animal models of disease can be employed were the long-term effect on nesting behaviors and specifically sorting behavior can be used in the method of the invention.

Sorting Activity Test Method

Applicants describe herein novel behavior tests based on observations of the behavior of the 3×Tg-AD mouse model of Alzheimer's disease described as a Sorting Activity Test (SAT). From as early as three-and-a-half to four weeks of age, the mice do not exhibit the typical "sorting" behavior observed in non-transgenic control mice derived from the same genetic background as the triple transgenic but which do not carry the transgenes (mixed background 129×C57BL/6) and other transgenic mice when housed with mixed-type bedding, such as AlphaCobb®.

Nesting is one the most basic activities for all animals and one that remains available to caged research subjects. The animal's natural nest and shelter building instincts can be accommodated within a laboratory cage by providing enrichment bedding material.

C57BL/6J mice are a standard, commercially available inbred strain, which have used in a number of studies with a focus on social components of behavior. For example, human Alzheimer's mutant β-amyloid precursor protein overexpressed in C57BL/6 breeder mice produces amyloid plaques in the brain and poor learning and memory on the Morris water task. The same transgenic insertion in FVB/N mice did not show plaque formation and was lethal at too young an age for learning and memory testing.

Numbers of transgenic animals and control animals for standardized experimental designs are appropriate for statistical tests. If a gender effect is detected, an appropriate number of each gender and each genotype is required. Ages of the animals are approximately equivalent across genotypes in accordance with the goals of the experiment. For example, mice are tested as "adult" when between ages 3 and 8 months; aged mice between 12 and 18 months; juvenile mice between 2 and 6 weeks (See Crawley, J. N. 1999. Behavioral phenotyping of transgenic and knockout mice: experimental design and evaluation of general health, sensory functions, motor abilities, and specific behavioral tests. Brain Research 835 (1): 18-26).

Preliminary observations of general health, home cage behaviors, sensory abilities, and motor functions may be first conducted for each mouse to avoid spurious false positives as animals with a health problem or a gross motor defect will be unable to perform many behavioral tasks for reasons not necessarily specific to the disease being modeled by the genetic mutation. The mouse is weighed, its body temperature is taken, and the appearance of its fur and whiskers is noted. Home cage locomotion, grooming, nesting, sleeping, and fighting patterns may be recorded. Neurological reflexes may also be used to assess gross defects in mutant mice such as eye blink, ear twitch, whisker twitch, and righting reflex. More complex motor and sensory skill tests may also be used such as the rotorod test or acoustic startle test. Such tests are well known to those skilled in the art of rodent behavioral testing.

Social behavior may be observed or tested in groups of rodents or individuals by periodic observation, by photographing, or by videotaping. Observations during the night are conducted under red light, which does not disturb the mice. Group huddling while sleeping is one characteristic of normal mouse social behavior. Fighting can be quantitated from the videotapes by scoring number and duration of attacks.

Oral shredding of bedding material is a sensorimotor behavior associated with nest building by both male and female rodents and, therefore, an important part of the rodent behavioral repertoire. In this test, pre-weighed cotton is made available to singly housed animals, each of which must pull the material from the bin. The time required to use the material is monitored at three to five time points over a 72-hour period. As the use of the cotton is dopamine dependent, and use reflects skilled digit use and motivation to nest build. This test has been used to evaluate models and treatment for Parkinson's disease, a movement disorder as well as a neurological deficit.

Animal Bedding Material

Animals housed in solid bottom cages, e.g., shoebox cages, may be provided bedding material which is absorbent. Corncob bedding products allow liquids to flow from the top down, then absorb from the bottom up. Corncob bedding products also offer ammonia control by encapsulating urea. Corncob bedding products are available under the names; Bed-O'Cobs®, in a variety of particle sizes such as 1/8" and 1/4" and a blend of both. The 1/4" size is most popular for mice as it provides a greater and more uniform surface area. Two pelleted noncontact products are also available; one with alfalfa and one plain corncob pellet.

Clean, dry corncobs, are precision ground to retain only the material from the woody ring of the cob. The cobs shall be heat treated to achieve moisture content not greater than 9% and to control any pathogenic bacteria. Fines content to be less than 1% through −20 screen. Typical final moisture after milling is 6% plus or minus 2. The drying process, including the temperature produced during the drying process, and the duration of time that the corncob is subjected to the highest temperature, may be specified. The bedding and litters may be provided as irradiated bedding or in autoclavable bags for sterilization. The corncob bedding product shall be within allowable limits of the following contaminants: fines, pesticides, heavy metals, toxins and any substance that might alter the results of biomedical research in laboratory animals. The production facilities shall be clean and vermin free to prevent the contamination of the bedding during the manufacturing process and are inspected annually by the National Institute of Health.

Paper only products are also available. One product is precision sized, e.g., 1/4" paper squares, such as Pure-O-Cel® (available from The Andersons, Inc., Maumee, Ohio). The 1/4" paper square, produced in an approved FDA facility, allows for more surface area to wick fluids. Another, such as Enrich-n'Pure® (available from The Andersons, Inc., Maumee, Ohio) is a blend of paper squares and twisted paper rolls which provides an enrichment material for mice and is the premium bedding material for toxicology research.

Enrichment bedding is bedding that provides the animals, specifically rodents, material that can be manipulated and moved, such as Enrich-O'Cobs®, which contains twisted paper rolls which are blended with a corncob bedding. The paper rolls can be unfurled, fluffed, and mounded into a sheltered nest for mice and their pups. Another type of enrichment bedding is a blend of corncobs and 1/4" paper square, such as AlphaCobb®. The product promotes activity with mice, separating the paper from the corncob particles.

Testing Methods

The methods of the present invention can be used to test for testing individual motivation if not memory and gross motor skill. In a particular method of the present invention, individual or groups of rodents are subjected to a behavioral evaluation for nesting behavior as exemplified by sorting of components of a bedding material made directly available to the individual or groups of rodents being tested. Rodents presented bedding having a nestable material, e.g., cotton squares, in admixture with less desirable nesting material, e.g., milled corncob, will separate the cotton from the cob in order to provide an area for nesting or nest-building. In one aspect of the invention, the sorting behavior observed can be scored and the scores used in a quantitative analysis of the behavior for the purposes of testing methods or substances for improving or restoring sorting behavior and, presumably, the underlying pathophysiological influence. A particular utility of the method of the invention has been found to be testing transgenic mice bearing genes related to human FAD such as $APP_{Swe}$ and $PS1_{M146V}$ and related to tauopathies, which include the $tau_{P301L}$ mutation. In one embodiment of the method of the invention, transgenic 129×C57BL/6 mice bearing human $APP_{Swe}$, human $PS1_{M146V}$ and $tau_{P301L}$ transgenes are used to test potential useful compounds for ameliorating, restoring, or preventing the loss of cognitive functions and adverse behavioral changes associated with AD by administering the test compounds to the transgenic mice and observing whether the sorting behavior score is increased as compared to transgenic mice not administered the test compound. Test agents are then selected based on the sorting behavior observations. The SAT method may also be used to evaluate possible adverse neurological effects and effects on mental abilities of therapeutic agents.

In the SAT test, rodents displaying altered sorting behavior are subjected to treatment (or the appropriate control treatments) which may comprise administration of a test compound, a specific test diet or dietary additive, or a physical treatment. The rodents cages are monitored for evidence of sorting behavior by providing enrichment bedding containing nestable material and observing the sorting of nestable material from non-nestable material. The observation of the sorting behavior is conveniently recorded periodically by direct observation or by recording the evidence of sorting behavior by a manually operated or automatically timed imaging device such as a digital camera. Thus, the behavior takes place independently of the observer and no operant or stimulus is required.

The behavior observation in the SAT can be made quantitative by applying a scoring system for the degree to which nestable material has been sorted from non-nestable material. The scoring system can have as few as two categories or as many as ten-categories of scores. Once scores have been recorded for groups of animals, appropriate statistical tests of the scores can be used to discern the level of significance of the difference in scoring behavior between groups of mice and thereby gauge the efficacy of the treatment, diet, or test compound.

Presently, the Irwin observation test is routinely used to assess physiologic effects of therapeutic compounds. The Irwin test can measure fear, aggressiveness, hyper-reactivity, and sedation. The observations cover a broad range of physiological systems, and can be completed quickly. This testing method is therefore a useful screen for the physiologic effects of compounds. However, there is no observation in the battery that indicates depression or cognitive loss. The Irwin test comprises several single test situations evaluating for general health, physiologic parameters and reflexes, and neuronal and behavioral abnormalities (Irwin Psychopharmacology 13(3): 222-257, 1968).

Several animal tests can be used to assess cognitive functions associated with depression. In addition to behavioral and cognitive tests described herein above, these tests include the forced swim, tail suspension, and learned helplessness tests. These models are useful and widely accepted, but they are time consuming and often complicated. Models for cognitive function, including the Morris water maze, and Operant Response, among others, are likewise cumbersome. The SAT method can be used separately or in conjunction with other screening methods, such as Irwin testing, to form a more complete picture of the neurological effects of therapeutic agents.

Substances Potentially Useful in Treating Neurological Disease

Compounds and compositions useful in treating neurological diseases having cognitive loss and exhibiting a behavioral component as described herein include any substance or composition capable of having an action which limits, prevents, or reverses the underlying pathology of the disease or which can compensate the pathophysiological changes in a manner causing a measurable change in the behavioral component.

Examples of such substances are large molecules such as antibodies particularly antibodies capable of sequestering or preventing A-beta aggregation, immunoglobulin-fusion proteins such as MIMETIBODIES™, biologics such as erythropoietin and erythropoietin stimulating agents (ESAs), small molecular compounds such as tricyclic antidepressants, selective serotonin reuptake inhibitors (SSRIs), serotonin-norepinephrine reuptake inhibitors (SNRIs), cholinesterase inhibitors, compounds suspected to prevent the reduction of synaptic transmission such as antioxidants, anti-epileptics, anti-diabetic compounds, and neuroactive agents.

The antibodies useful in the method of the invention can be prepared in several ways well known in the art. Antibodies may be directed to disease-inducing targets, e.g., anti-APP or anti-A-beta antibodies or be directed to the therapeutics administered to treat disease or depression, e.g., anti-imipramine antibodies such as for use in overdosage treatment. Any disease-modifying antibody may be tested in the method of the invention.

Natural or synthetic oligo- or polynucleotides designed to knock-down or knock-out gene expression or prevent or limit the translation of a specific gene product may be tested in the method of the present invention such as siRNA, shRNA, antisense RNA, and the like.

While having described the invention in general terms, the embodiments of the invention will be further disclosed in the following non-limiting examples.

EXAMPLE 1

Sorting Behavior in an AD Model

The 3xTg-AD mice developed by LaFerla et al., at the University of California at Irvine (Neuron 2003b) were used in the study. These mice harbor mutations in three different genes: the β-amyloid precursor protein ($APP_{SweKM \rightarrow NL}$), presenilin-1 ($PS1_{M146V}$) and tau (P301L). Reports show, the mice exhibit both plaque and tangle pathology in brain regions relevant to AD, such as hippocampus and cortex. Intracellular A-beta peptide immunoreactivity has been reported to appear by as early as three months of age and extracellular A-beta deposits in evidence between six and 12 months of age (Oddo et al., 2003a, 2003b). In the cohort of mice used in the present studies, these hallmarks of AD were not observed until 19 months of age by immunohistochemical methods.

The goal of these studies was to examine the sorting behavior of both non-transgenic control and triple transgenic mice, and begin to elucidate its cause. In two separate studies, mice were housed in pairs, and their sorting behavior observed. In one study, anti-beta-amyloid mAbs were administered to determine if elevated levels of beta-amyloid are implicated in this behavioral pattern. Besides cognitive deficits, Alzheimer's disease has many peripheral symptoms, including depression. Therefore, the effect of anti-depressant compounds, desipramine and imipramine, was also studied.

Triple transgenic (3xTg-AD) mice and corresponding non-transgenic control mice were weaned and group housed four (4) mice per cage in large static microisolator caging composed of a tinted polycarbonate cage, stainless steel lid, and polycarbonate filtered top at Ace Animals, Inc. Mice were fed 5% Fat Purina Autoclavable Breeder Diet (Item #RHI5R24CGP) and provided reverse osmosis chlorinated water ad libitum within a barrier environment in an environmentally controlled facility (22° C., 40-60% relative humidity) with a 12:12-hour light: dark cycle. Health status reports certify that all animals were free of known viral, bacterial, and parasitic pathogens.

The unique factor within this colony was the use of a combination corncob and papered bedding (AlphaCobb® cat #ALPHA4B, Animal Specialties and Provisions, Quakertown, Pa.). The mice were 8 weeks of age at the start of the study.

Imipramine and desipramine are in the tricyclic class of antidepressants which acts by inhibiting the reuptake of several neurotransmitters in the brain. It was first approved for the treatment of depression in 1959. It is currently sold as Antideprin®, Imipramil, and Tofranil®, among others. Desipramine is an active metabolite of imipramine that inhibits the reuptake of norepinephrine. It is sold under the brand names Norpramin® and Pertofrane®. The advent of second-generation antidepressants, selective serotonin reuptake inhibitors (SSRIs), have decreased the clinical use of these medications. Tricyclic antidepressants are frequently used in animal models of depression. In mouse models, they are typically dosed intraperitoneally at 20-30 mg/kg. Dosing can be acute or chronic. Desipramine (cat #D3900) and imipramine (cat #17379) were purchased from Sigma-Aldrich Co., St. Louis, Mo.

Mice were housed 2 per cage, 6 cages per group: Non-transgenic control, untreated, 3xTg-AD, untreated, 3xTg-AD, Desipramine, 30 mg/kg, and 3xTg-AD, Imipramine. All mice were approximately two months of age at the start of the study. Mice were dosed once daily, Monday through Friday with test article. Cages were photographed weekly on Day 7, and cage bedding was changed once per week after photographs were taken.

Sorting Behavior

Although the early plaque pathology described by Frank LaFerla et al., was not reproduced in-house, an interesting behavior was observed at facility where the mice were housed. Non-transgenic control mice, when housed with a mixed-type bedding such as AlphaCobb™, a mixture of Alpha-Dri™ and Cob Blend™, will sort and separate the two types of material found in the bedding. It was observed that 3xTg-AD mice lose interest in sorting of the AlphaCobb™ bedding in their cages at a very early age compared to non-transgenic control mice. The relevance of this behavior difference was not known.

In order to quantify the sorting behavior of the mice in this study, a scoring system was devised. Before the start of the initial study the mice were observed. It was evident that the sorting behavior was not an "all or nothing" phenomenon, but rather existed in degrees. After observing the cages for some time, scoring criteria were established.

A score of 0 was given to cages that showed no sorting behavior after 7 days. In these cages, the two types of bedding were equally mixed throughout the cage. There was no area where one bedding type was more concentrated.

A score of 1 was given to cages that showed a slight degree of sorting. In these cages, a small area of white bedding was seen, usually piled in a corner. The two types of bedding were equally mixed throughout the rest of the cage.

A score of 2 was given to cages when the white area of bedding was more pronounced, yet the bedding throughout the rest of the cage was still mixed.

A score of 3 was given to cages when the white area was very clearly defined, and very little white bedding was left mixed with the Alpha Cobb.

A score of 4 was given to cages when the two types of bedding were almost completely separated from each other.

The degree of sorting at the end of each 7 day period (before the cages were changed) was scored using this system.

Using the scoring system devised and making daily observations of the cages, the behavior patterns of the non-transgenic control mice could be clearly distinguished from the 3xTg-AD mice within a matter of a couple days, but was most prominent after Day 3. At Day 7 before each bedding change, the bedding of each cage was digitally photographed and scored. Table 1 provides the mean score and standard deviation (SD) for each group of mice for each week observed.

TABLE 1

| WEEK | NON-TRANSGENIC | | 3XTG-AD, UNTREATED | | 3XTG-AD, DESIPRAMINE | | 3XTG-AD, IMIPRAMINE | |
|---|---|---|---|---|---|---|---|---|
| | MEAN | SD | MEAN | SD | MEAN | SD | MEAN | SD |
| 1 | 2.83 | 0.75 | 0.50 | 0.84 | 0.00 | 0.00 | 0.00 | 0.00 |
| 2 | 1.33 | 0.52 | 0.00 | 0.00 | 0.50 | 0.84 | 0.67 | 0.82 |
| 3 | 3.00 | 0.63 | 0.00 | 0.00 | 1.17 | 0.75 | 0.17 | 0.41 |
| 4 | 2.67 | 0.82 | 0.00 | 0.00 | 0.83 | 0.98 | 0.33 | 0.52 |
| 5 | 2.17 | 1.17 | 0.17 | 0.41 | 0.83 | 0.98 | 0.33 | 0.52 |
| 6 | 2.50 | 1.05 | 0.17 | 0.41 | 0.50 | 0.84 | 0.33 | 0.52 |
| 7 | 2.50 | 1.52 | 0.17 | 0.41 | 0.83 | 0.98 | 0.33 | 0.82 |

The non-transgenic mice sorted bedding throughout the course of the study. The untreated 3xTg-AD mice showed little sorting activity in the initial week of the study (mean score of 0.50), which decreased thereafter. The desipramine treated 3xTg-AD mice showed little sorting in the initial week of the study but regained some of the behavior as compared to the untreated Tg mice thereafter.

Table 2 shows the mean score for each group over the course of the study. Data was analyzed using GraphPad Prism software with ANOVA one-way analysis of variance followed by Dunnett's multiple comparison test. All groups (6 cagesx7 weeks) were compared to untreated 3xTgAD group. Significance was defined as $p<0.05$. The averaged day 7 post-bedding change sorting score for both the desipramine-treated and the imipramine-treated groups of mice and the 3xTg-AD untreated control group were significantly different from untreated Tg mice for desipramine, at $p<0.01$ level and imipramine at $p<0.05$.

TABLE 2

| GROUP | N | MEAN | SD | P |
|---|---|---|---|---|
| NON-TRANSGENIC | 42 | 2.43 | 1.04 | <0.01 |
| 3XTG-AD UNTREATED | 42 | 0.14 | 0.42 | |
| 3XTG-AD + DESIPRAMINE | 42 | 0.67 | 0.85 | <0.01 |
| 3XTG-AD + IMIPRAMINE | 42 | 0.31 | 0.56 | <0.05 |

The sorting activity test (SAT) involves generating a scoring of observed behavior related to sorting of nestable versus non-nestable bedding components by 3xTg-AD mice which are known to exhibit pathophysiological changes characteristic of Alzheimer's Disease. Therefore, the loss of sorting behavior in mice may be analogous to the behavioral and psychological symptoms of dementia seen in AD patients and may derive from the pathophysiology caused by the human transgenes.

The study suggests that desipramine had a greater effect than imipramine, on the 3xTg-AD mice with respect to their behavior for sorting the bedding material. As desipramine and imipramine are neuroactive agents which have been used in human patients as antidepressants, this supports the use of sorting behavior as a useful as a readout for testing compounds that affect neuronal pathways.

EXAMPLE 2

Effect of Anti-Beta-Amyloid Mab on Sorting Behavior

Mice were housed 2 per cage, 6 cages per group. All mice were approximately two months of age at the start of the study. Mice were dosed weekly with test agent. All test agents were administered at 25 mg/kg, intraperitoneally. Cages were photographed 3 times weekly, and cage bedding was changed once per week.

CNTO2125 is a murine monoclonal antibody of the $IgG_1$ isotype, created using to human A-beta peptide residues 1-7 (anti-N terminal Aβ) and CNTO4010 is a murine monoclonal antibody of the IgG1 isotype created by immunization of human A-beta peptide residues 35-40 (anti C-terminal $Aβ_{40}$) as described in US Patent Application number US20050129695A1 (now abandoned). The mice were divided into 4 groups as follows:

| GROUP 1 | NON-TRANSGENIC + CNTO151 ($IGG_1$ ISOTYPE CONTROL MAB) |
| GROUP 2 | 3XTG-AD + CNTO151 ($IGG_1$ ISOTYPE CONTROL MAB) |
| GROUP 3 | 3XTG-AD + CNTO2125 (ANTI N-TERMINAL Aβ) |
| GROUP 4 | 3XTG-AD + CNTO4010 (ANTI C-TERMINAL $Aβ_{40}$) |

The study was conducted over a 12-week period. Digital photos of each mouse cage were taken four times per week during the course of the study on (Days 1, 3, 4 and 7 after being placed in the cage). Photos on day 7 were scored on a scale of 0-4 based on the degree of sorting as described in Example 1. Photos were scored by three different individuals and averaged.

The mean sorting scores for mice in each test group are shown in Table 3 below. The control antibody-treated 3xTg-AD group demonstrated almost no sorting behavior during the course of the study. Some of the CNTO2125-treated 3xTg-AD groups showed sorting activity. The CNTO4010-treated 3xTg-AD group showed very little sorting behavior. The scores for each group remained consistent after week 4. The scores for the antibody-treated mice were significantly higher than for the untreated 3xTg-AD mice (CNTO2125, $p<0.01$, CNTO4010, $p<0.05$).

TABLE 3

| | NON-TRANSGENIC, CNTO151 | | 3XTG-AD, CNTO151 | | 3XTG-AD, CNTO2125 | | 3XTG-AD, CNTO4010 | |
|---|---|---|---|---|---|---|---|---|
| WEEK | MEAN | SD | MEAN | SD | MEAN | SD | MEAN | SD |
| 1 | 3.33 | 0.52 | 0.33 | 0.52 | 0.17 | 0.41 | 0.33 | 0.52 |
| 2 | 3.33 | 0.82 | 0.33 | 0.52 | 0.50 | 0.84 | 0.33 | 0.52 |
| 3 | 3.33 | 0.82 | 0.00 | 0.00 | 0.33 | 0.52 | 0.17 | 0.41 |
| 4 | 2.67 | 0.82 | 0.00 | 0.00 | 0.50 | 0.55 | 0.17 | 0.41 |
| 5 | 3.50 | 0.55 | 0.33 | 0.52 | 0.67 | 0.82 | 0.17 | 0.41 |
| 6 | 2.67 | 1.03 | 0.17 | 0.41 | 0.50 | 0.84 | 0.33 | 0.52 |
| 7 | 3.50 | 0.84 | 0.17 | 0.41 | 0.50 | 0.84 | 0.17 | 0.41 |
| 8 | 2.50 | 0.55 | 0.00 | 0.00 | 0.50 | 0.84 | 0.33 | 0.52 |
| 9 | 3.67 | 0.52 | 0.17 | 0.41 | 0.50 | 0.84 | 0.33 | 0.52 |
| 10 | 3.17 | 0.75 | 0.00 | 0.00 | 0.33 | 0.82 | 0.00 | 0.00 |
| 11 | 2.83 | 0.75 | 0.00 | 0.00 | 0.50 | 0.84 | 0.17 | 0.41 |

Table 4 shows the mean score for each group over the course of the study. Data was analyzed using GraphPad Prism software with ANOVA one-way analysis of variance followed by Dunnett's multiple comparison test. All groups (6 cages×11 weeks) were compared to untreated 3×Tg-AD group. Significance was defined as p<0.05.

TABLE 4

| GROUP | N | MEAN | SD | P |
|---|---|---|---|---|
| NON-TRANSGENIC, CNTO151 | 66 | 3.14 | 0.78 | <0.01 |
| 3XTG-AD, CNTO151 | 66 | 0.14 | 0.35 | |
| 3XTG-AD, CNTO2125 | 66 | 0.45 | 0.71 | <0.01 |
| 3XTG-AD, CNTO4010 | 66 | 0.23 | 0.42 | >0.05 |

The administration of a Mab directed to the N-terminal region of beta-amyloid protein is active in restoring behavior normally observed in mice, sorting of nestable bedding material, in transgenic mice expressing three human transgenes associated with pathologies seen in Alzheimer's Disease patients.

What is claimed:

1. A method of identifying and selecting an agent for use in the prevention, treatment, or amelioration of a condition selected from the group consisting of Alzheimer's disease and a tau pathology, using a transgenic mouse whose genome comprises mutant nucleic acids that encode the Swedish mutant form of human amyloid precursor protein (hAPP), the $PS1_{M146V}$ mutant form of presenilin-1, and the P301L mutant form of tau, wherein the transgenic mouse exhibits decreased sorting behavior compared to a non-transgenic mouse of the same strain, the method comprising the steps of:

a) providing a number of said transgenic mice;
b) dividing the mice into a test group and a control group and providing each with sortable material;
c) administering a test agent to mice in said test group and administering a control agent to mice in said control group;
d) observing the mice in said test group and said control group for sorting behavior;
e) assessing the sorting behavior, wherein a decrease in sorting behavior in the test group, as compared to the control group, is indicative of Alzheimer's disease or a tau pathology, and an increase in sorting behavior in the test group, as compared to the control group, is indicative of amelioration of symptoms associated with Alzheimer's disease or a tau pathology; and f) selecting a test agent that produces an increase in sorting behavior in the test group, as compared to the control group, as an agent for trestment of Alzheimer's disease or a tau pathology.

2. The method of claim 1 wherein a reduction in sorting behavior is coincident with a histopathological marker present in the transgenic mice.

3. The method of claim 2 wherein the severity of the histopathological marker produces a phenotype that is decreased coincident with the exhibition of an increase in sorting behavior in the transgenic mice.

4. The method of claim 2 wherein the histopathological marker is selected from the group consisting of compacted plaques, neuritic dystrophy, gliosis, A-beta deposits, decreased synaptic density, and synaptic abnormalities.

5. The method of claim 1, wherein a predetermined scoring system is applied to each observation of the sorting behavior and the scores obtained using said scoring system are subjected to statistical analysis to determine whether the differences in sorting behavior between test and control groups is statistically significant.

6. The method of claim 1, wherein the test agent comprises a substance selected from the group consisting of an antibody, a fusion protein, a therapeutic protein, a small-molecule neuroactive, an antidiabetic agent, an oligonucleotide, and a dietary supplement.

* * * * *